United States Patent [19]

Pflueger et al.

[11] Patent Number: 4,991,588

[45] Date of Patent: Feb. 12, 1991

[54] DOPPLER GUIDE WIRE

[75] Inventors: D. Russell Pflueger, Newport Beach; Cliff N. Cottonaro, Trabuco Canyon; Scott M. Evans, Tustin, all of Calif.

[73] Assignee: Pfizer Hospital Products Group, Inc., New York, N.Y.

[21] Appl. No.: 434,590

[22] Filed: Nov. 13, 1989

Related U.S. Application Data

[63] Continuation of Ser. No. 224,206, Jul. 22, 1988, abandoned, which is a continuation of Ser. No. 887,291, Jul. 21, 1986, abandoned.

[51] Int. Cl.5 ............................................. A61B 8/12
[52] U.S. Cl. ................................... 128/662; 128/772
[58] Field of Search ..................... 124/344, 348.1, 305, 124/772, 660–661, 663, 692, 642

[56] References Cited

U.S. PATENT DOCUMENTS

| | | |
|---|---|---|
| 3,789,841 | 2/1974 | Antoshkiw . |
| 4,527,569 | 7/1985 | Kolb . |
| 4,538,622 | 9/1985 | Samson et al. . |
| 4,545,390 | 10/1985 | Leary . |
| 4,576,177 | 3/1986 | Webster, Jr. ........................ 128/660 |
| 4,580,573 | 4/1986 | Quinn . |
| 4,582,067 | 4/1986 | Silverstein et al. ................. 128/663 |
| 4,587,972 | 5/1986 | Morantte, Jr. ...................... 128/660 |
| 4,589,419 | 5/1986 | Laughlin et al. ................... 128/663 |
| 4,665,925 | 5/1987 | Miller ................................. 128/663 |

OTHER PUBLICATIONS

Wells, P. N. T., "Biomedical Ultrasonics", 1977 Academic Press, London, pp. 52–53.

Hisanaga, K. et al., "A New Trans-Digestive Tract Scanner", Proc. 23rd AIUM 1978, p. 1705.

Baba, K., "UTS Diagnostic Apparatus", Europ. Patent Appln, EP 0065275 Publ. 11-1982.

C. J. Hartley and J. S. Cole, "An Ultrasonic Pulsed Doppler System for Measuring Blood Flow in Small Vessels", J. Appl. Physiol, 37(4), 1974.

Primary Examiner—Francis Jaworski
Attorney, Agent, or Firm—Peter C. Richardson; Robert F. Sheyka; Thomas C. Naber

[57] ABSTRACT

A guide wire for an intravascular catheter is disclosed. In one embodiment, the guide wire has Doppler means positioned on the distal end, with preferred Doppler means being piezoelectric ceramics or piezoelectric polymeric materials, both having electrical leads connected thereto. In another embodiment, the guide wire has a Laser Doppler means.

10 Claims, 3 Drawing Sheets

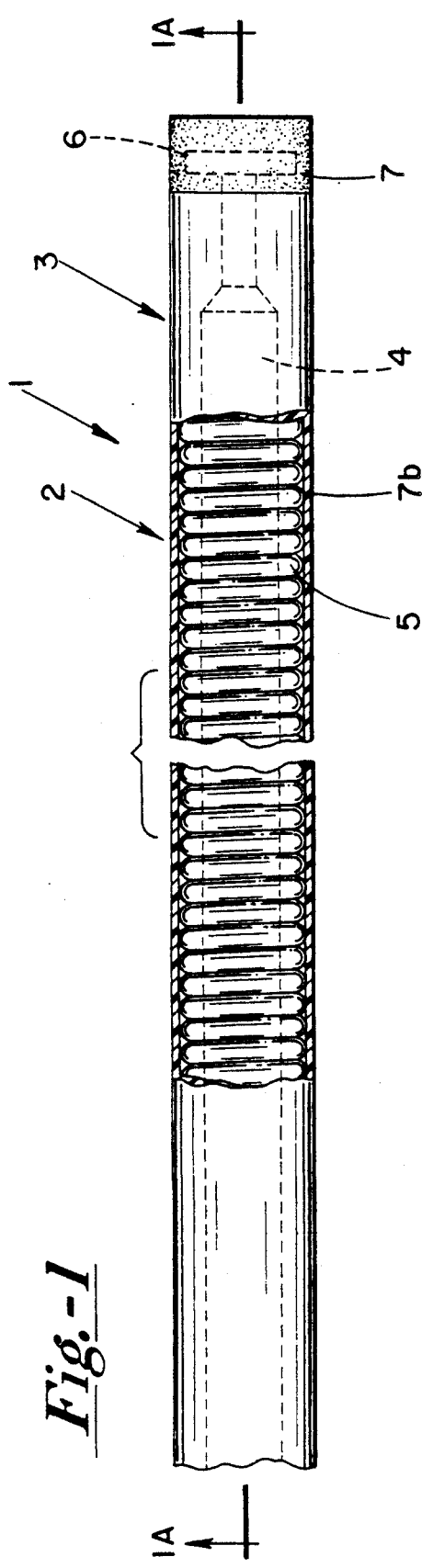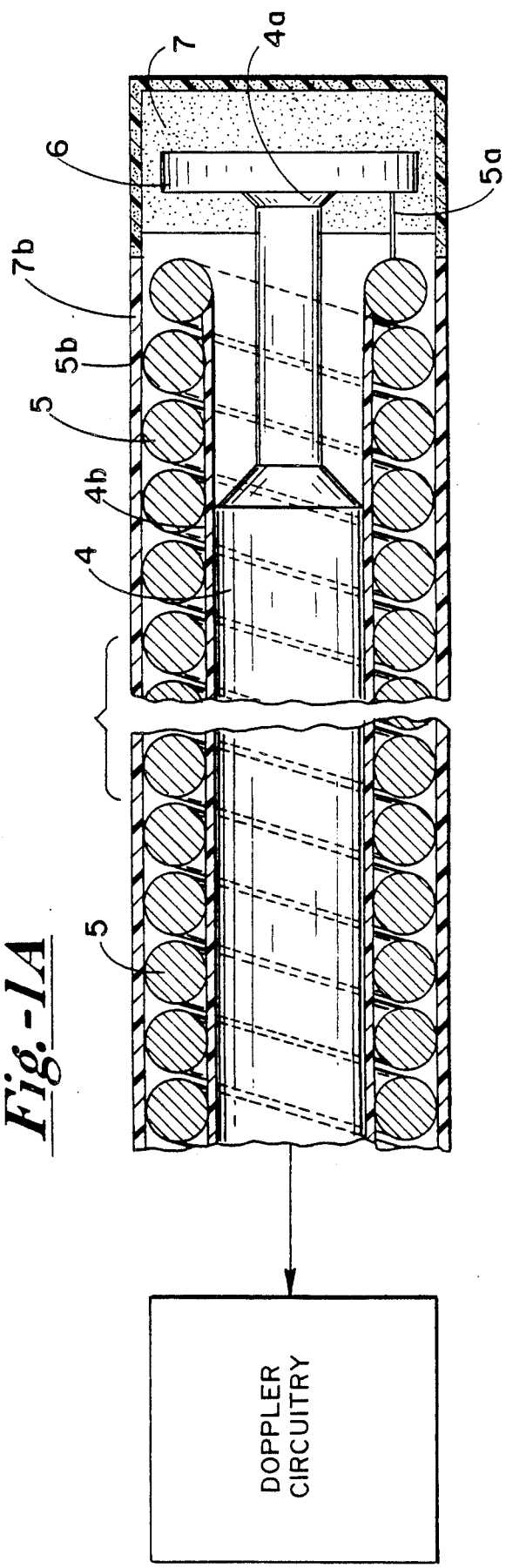

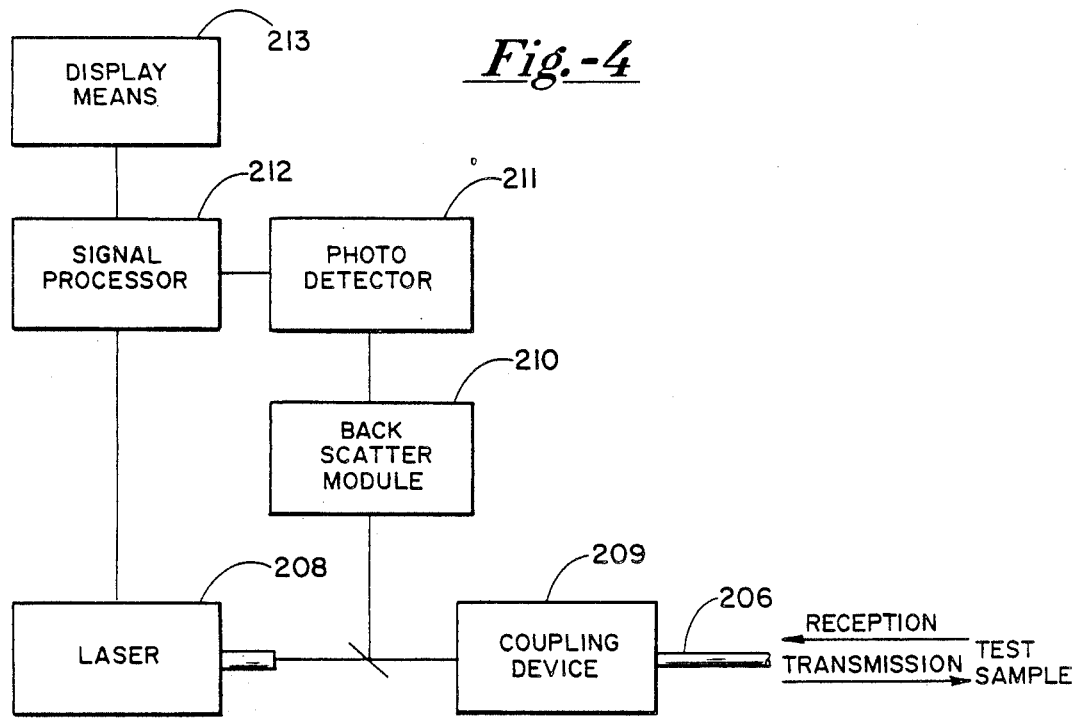
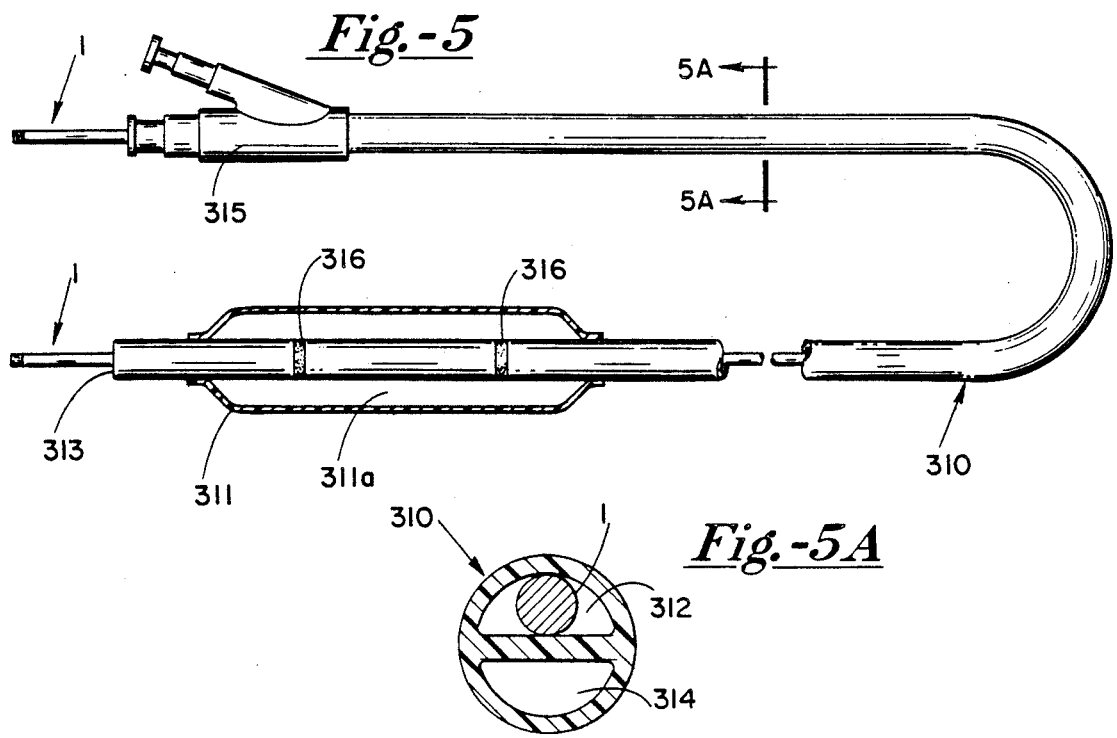

DOPPLER GUIDE WIRE

This is a continuation of application Ser. No. 224,206, filed on July 22, 1988, and now abandoned, which in turn is a continuation of Ser. No 887,291 filed on July 21, 1986, and now abandoned.

BACKGROUND OF THE INVENTION

The present invention relates to a guide wire for an intravascular catheter. More particularly, the present invention relates to a guide wire having a Doppler means positioned thereon.

With the recent marked advances in cardiac and vascular surgery, the use of cardiac and vascular catheters has increased considerably. Since these catheters must be inserted over a relatively long distance into internal sites in the body, considerable manipulation is required to maneuver a relatively long catheter into branch vessels that extend at sharp angles relative to the feeding direction of the catheter.

The most common catherization procedure is the Seldinger technique wherein an area of the skin is antiseptically prepared and a local anesthetic is applied, after which a small cut is made in the skin over the site of the vessel to be cannulated. An arterial needle assembly (inner needle, stylet) is then introduced into the vessel and its introduction is indicated by a back flow of blood to the inner needle. The inner needle is then withdrawn and replaced with a guide wire which is then introduced through a cannula for a distance of approximately 6 to 10 inches. External pressure is then applied to hold the guide wire in place while the cannula is withdrawn after which the guide wire is fed into the vessel to the selected area by fluoroscopy or some other similar technique. Considerable manipulation is required of the guide wire to direct it to the desired area. Once the guide wire reaches the selected area, the catheter is passed over the guide wire to the selected area after which the guide wire is withdrawn from the catheter. In angioplasty procedures, the technique employed is similar, however, the guide wire is not withdrawn.

Generally, the guide wires used to locate the catheter are formed of closely wound stainless steel or gold wire forming a continuous coil spring having an inner bore which is sealed at the distal end with a rounded cap or tip. Various modifications of this basic design are disclosed in, for example, U.S. Pat. Nos. 3,789,841, 4,538,622, 4,545,390 and 4,580,573.

U.S. Pat. No. 4,527,569 discloses a device for guiding a surgical needle into a blood vessel. The disclosed device contains one piezoelectric transducer acting as a transmitter and the other piezoelectric transducer acting as a receiver and requires that the transducers be aligned such that there is a point of convergence between the axis of the ultrasonic beam produced by the first transducer and the line of sight along which the second transducer receives reflected waves. The disclosed device is stated to be useful for the first part of the Seldinger technique wherein the surgical needle is introduced into the blood vessel but no mention is made of the use of the device for the introduction of the guide wire or catheter.

SUMMARY OF THE INVENTION

In one embodiment, the present invention is directed to a guide wire for use in advancing a catheter into a blood vessel or a body cavity comprising (a) an elongated body having a distal portion and (b) Doppler means for transmitting a signal and for receiving a reflected signal from said blood vessel or body cavity, said Doppler means comprising a single piezoelectric transducer attached to said elongated body adjacent said distal portion and having electrical leads operably connected to said transducer. In one preferred embodiment, the body of the guide wire is a helically coiled element. In another embodiment, the body of the guide wire is comprised of a relatively straight central element surrounded by a helically coiled element. In yet another embodiment, the central element and the helically coiled element are comprised of a conductive material with both elements serving as electrical leads to the piezoelectric transducer. A preferred range for the diameter of the guide wire is from 0.010 to 0.065 inches with a preferred diameter of 0.014 inches.

In another preferred embodiment, the Doppler means is a pulsed Doppler wherein a single element alternately acts as a transmitter and a receiver with a preferred piezoelectric transducer being a lead-zirconium-titanate ceramic. Another preferred piezoelectric transducer is a piezoelectric polymeric transducer with an especially preferred polymer being polarized polyvinylidene fluoride (PVDF). The piezoelectric transducer can be radially or axially oriented in relation to said elongated body of the guide wire, and in addition, can be constructed so as to transmit ultrasonic energy in a radial or longitudinal direction.

In still another preferred embodiment, the present invention is directed to a guide wire for use in advancing a catheter into a blood vessel or a body cavity comprising (a) an elongated body forming a sheathing means and (b) Doppler means for transmitting a signal and for receiving a reflected signal from said blood vessel or body cavity, said Doppler means comprising at least one light transmitting fiber capable of transmission and reception of light signals, said light transmitting fiber being encased by said sheathing means. In a preferred embodiment, the light transmitting fiber is adapted to transmit light from a laser source at a wavelength of about 1 Kilohertz to about 100 Megahertz, particularly a helium-neon laser.

In yet another embodiment, the present invention is directed to a set for introducing a balloon dilatation catheter comprising a guide wire incorporating any of the previously described Doppler means and a balloon dilatation catheter receptive to said guide wire.

BRIEF DESCRIPTION OF THE DRAWINGS

FIG. 1 depicts the guide wire of the present invention shown in a side view.

FIG. 1a depicts a longitudinal sectional view of the guide wire of FIG. 1 taken along line 1a–1a.

FIG. 4 depicts the circuitry controlling the laser Doppler means of FIG. 3.

FIG. 5 depicts a dilatation catheter in combination with the guide wire of the present invention.

FIG. 5a is a cross sectional view taken along line 5a–5a of FIG. 5 and depicts the guide wire of the present invention in place in the dilatation catheter.

DETAILED DESCRIPTION OF THE INVENTION

Figure 2:
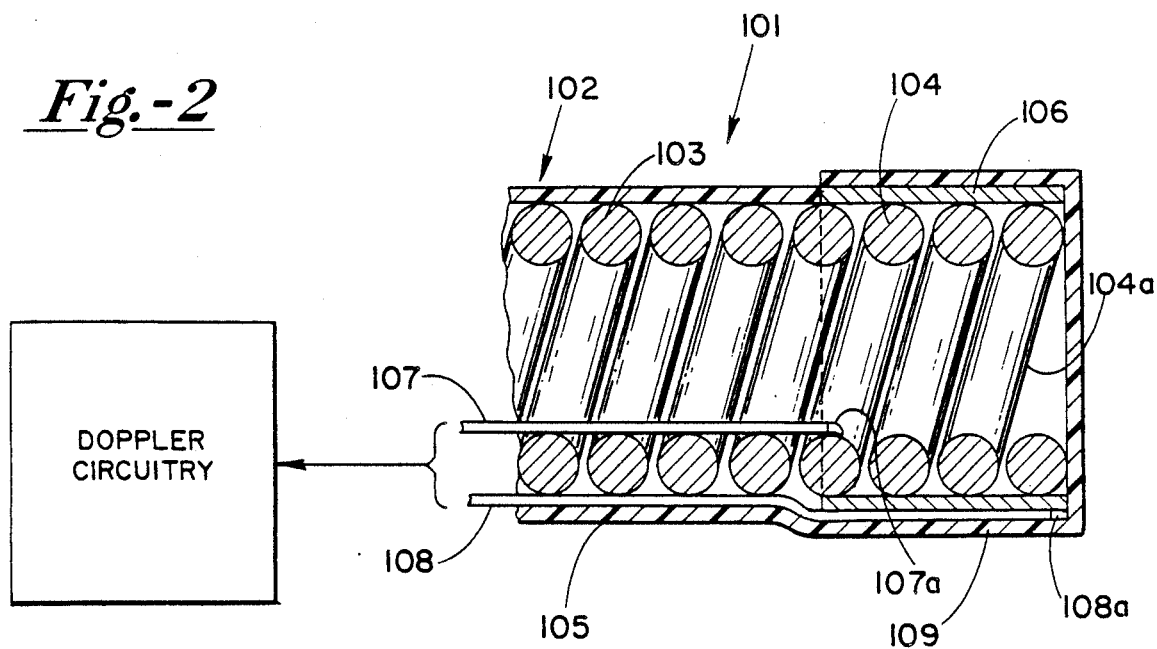
FIG. 2 depicts an alternative embodiment of the guide wire of the present invention.

From FIG. 1, it can be see that a guide wire 1 of the present invention comprises an elongated body 2 surrounded by a helically coiled element 5. Elongated body 2 has a distal portion 3. Attached to distal end of distal portion 3 is piezoelectric transducer 6. In the embodiment shown in FIG. 1a, elongated body 2 is comprised of a relatively straight central element 4 which is surrounded by a helically coiled element 5. In a preferred embodiment, both central element 4 and helically coiled element 5 are comprised of a conductive material, for example, gold, silver, copper and other conductive alloys.

Attached to the distal portion 3 of elongated body 2 is piezoelectric transducer 6. Piezoelectric transducer 6 is secured to distal portion 3 of elongated body 2 by the application of a non-porous and electrically insulating material 7, such as an epoxy resin. Electrically insulating material 7 serves to electrically insulate piezoelectric transducer 6 from any fluid, e.g. blood, into which guide wire 1 is inserted.

Guide wire 1 shown in FIG. 1a is designed so that central element 4 and helically coiled element 5 are comprised of conductive material, thus serving as electrical leads to piezoelectric transducer 6. Central element 4 is operably connected, for instance, by soldering, to piezoelectric transducer 6 at connecting point 4a. Similarly, helically coiled element 5 is operably connected, for instance, by soldering, to piezoelectric transducer 6 at connecting point 5a Both central element 4 and helically coiled element 5 are operably connected to external Doppler circuitry (not shown). Electrically insulating material 7 also serves to insulate connecting points 4a, 5a from contact with body fluids. To further minimize the possibility of electric shocks to the patient, the outside surface 4b of central element 4 and the outside surface 5b of helically coiled element 5 are also coated with an electrically insulating material 7b, for example, a non-conductive polymer.

The piezoelectric transducer 6 which is attached to the distal end of elongated body 3 in combination with the electrical leads (central element 4 and helically coiled element 5 of FIG. 1a) and Doppler circuitry form part of a Doppler means which can be used for the detection of various pathological conditions including arterial stenoses, air emboli, aneurysms, etc. as well as measuring normal parameters, such as blood velocity.

In a preferred embodiment, the piezoelectric transducer 6 is a piezoelectric ceramic crystal comprising a lead-zirconium-titanate material which is about 0.004 inch in longitudinal thickness and 0.014 inch in outside diameter. The piezoelectric transducer 6 is designed to resonate at a range of from 10 to 20 megahertz with a voltage applied to generate a 10 to 20 megahertz signal. The piezoelectric transducer 6 is preferably a single transducer to operate as a pulsed Doppler, acting alternately as transmitter and receiver. The use of a pulsed Doppler system for measuring blood flow in small vessels is detailed in the article by C. J. Hartley and J. S. Cole entitled "An Ultrasonic Pulsed Doppler System for Measuring Blood Flow in Small Vessels" appearing in J. Appl. Physiol. 37(4), 1974.

In another preferred embodiment, the piezoelectric transducer 6 is a piezoelectric material which is an electret of high polymeric material or which is an electret of a composite consisting of a high polymeric resin and a piezoelectric ceramic, each of the above being defined as a piezoelectric polymeric material.

Piezoelectric polymeric materials can be used in the form of electrets obtained by a manufacturing method which comprises stretching films or extrusions of thermoplastics such as polyvinyl fluoride, polyvinylidene fluoride, polyvinyl chloride, polyacrylonitrile, polycarbonate etc., to several times their original length while at a temperature near the softening temperature, forming electrodes on both surfaces of the resulting stretched film or extruded material either by vapor deposition of silver, gold, or aluminum or by chemical plating, with the heating from room temperature to the temperature near the softening point being accomplished under a condition of applied electric field of from about 100 to about 700 KV/cm DC, and then cooling the product.

Alternatively, as a piezoelectric polymeric material, suitable electrets can be obtained by manufacturing a composite which comprises mixing from 90 to 10% by volume of piezoelectric ceramics with from 10 to 90% by volume thermoplastic resin. The thermoplastic resin is a crystalline and polar resin such as polyacetal, vinylidene fluoride resin, or polyamide. Alternatively, the electrets can be obtained by manufacturing a composite which comprises mixing from 90 to 10% by volume piezoelectric ceramics with from 10 to 90% by volume of a blend polymer. The blend polymer is obtained by blending 99 to 20% by weight of the thermoplastic resin and 1 to 80% by weight of a polar polymer such as chloroprene rubber, acrylonitrile butadiene rubber, epichlorohydrin rubber, chlorinated polyethylene and urethane rubber. The resulting composite is then molded into a film of 5-500 um thickness. The molded composite is heated from about 400° C. to about 1000° C. after forming metal layers on its opposite sides by vapor depositing or plating silver or aluminum, and applying thereto an electric field of direct current above 50 amps. Thereafter, the molded composite is cooled.

If the piezoelectric ceramic employed is a lead-zirconium-titanate ceramic, a typical manufacturing process comprises adding from 10 to 90% by volume of the thermoplastic resin to a lead-zirconium-titanate ceramic solution of about 0.2 to 45 um diameter, molding the resulting composite, forming the electrodes on the surface and electretizing the resulting molded composite. The piezoelectric polymeric material is cut to an appropriate size and adhered to the guide wire. The mounting of the piezoelectric polymeric material is as illustrated in FIG. 1a with the electrically insulating material 7 encapsulating the piezoelectric polymeric material and central element 4 and helically coiled element 5 serving as electrical leads to the piezoelectric polymeric material. While the piezoelectric transducer depicted in FIG. 1 is axially oriented in relation to the elongated body 2 of the guide wire 1, it is to be understood that axial orientation is not absolutely necessary. The piezoelectric transducer can also be constructed so that the transmission of ultrasonic energy is either in a longitudinal or radial direction relative to the longitudinal axis of the guide wire.

FIG. 2 depicts an alternative embodiment of the guide wire of the present invention. In this embodiment, guide wire 101 is comprised of an elongated body 102 comprising a helically coiled element 103 having a distal portion 104. In this embodiment, guide wire 101 does not have the relatively straight central element 4 shown in FIG. 1a. Preferably, helically coiled element 103 is covered with insulating material 105. Located at the distal end 104a of distal portion 104 of helically coiled element 103 is piezoelectric transducer 106. Electrical leads 107, 108 are connected to piezoelectric transducer 106 at points 107a, 108a with piezoelectric transducer 106, electrical leads 107, 108, and connecting points 107a, 108a insulated by an electrically insulating material 109 similar to that previously described. In FIG. 2, electrical leads 107, 108 are depicted as running along the inner surfaces of elongated body 102 to Doppler circuitry (not shown). Since electrical leads 107, 108 are insulated, it will be readily appreciated that they can also run along the outer surfaces of elongated body 102 or be coiled about the outer surface of elongated body 102. Piezoelectric transducer 106 may also be comprised of any of the piezoelectric ceramic or piezoelectric polymeric materials previously described.

Figure 3:
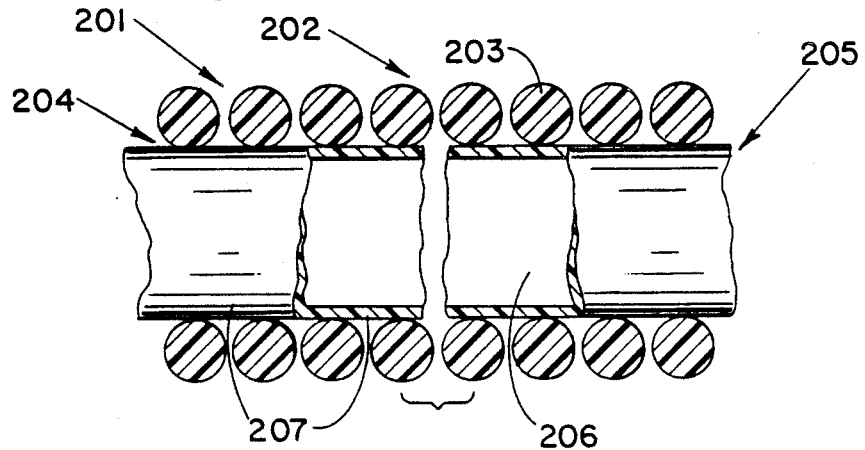
FIG. 3 depicts an alternative embodiment of the guide wire of the present invention wherein the Doppler means is a laser Doppler means.

FIG. 3 depicts another embodiment of the guide wire of the present invention. From FIG. 3, it can be seen that guide wire 201 comprises an elongated body 202 consisting of an insulated helically coiled element 203 having a proximal portion 204 and a distal portion 205 with proximal portion 204 and distal portion 205 configured so as to form a sheathing means. Within elongated body 202 and surrounded by helically coiled element 203 is optical fiber 206 supported within helically coiled element 203 by an outer sleeve 207. Suitable materials of which outer sleeve 207 may be comprised include flexible plastics and other flexible polymers.

FIG. 4 depicts a Laser Doppler mechanism of the guide wire of FIG. 3. From FIG. 4, it can be seen that laser 208 transmits light through coupling device 209 from which the light is transmitted through fiber 206 to the test sample. In the practice of the present invention, it is preferred that the Laser Doppler means be operated in the backscatter mode wherein the transmitted signal reflects off objects in the test sample, for example blood cells, or air emboli. In this case, the reflected signal goes to optical fiber 206 which then sends the signal back to backscatter module 210. The received signal from backscatter module 210 is then sent to photodetector 211, to signal processor 212 for comparison to the transmitted signal and finally to display means 213.

Laser source 208 can be any laser source capable of generating light at a wavelength of from from about 1 Kilohertz to about 100 Megahertz. Examples of such lasers include helium-neon lasers, argon-ion lasers, krypton and helium-cadmium lasers. Coupling means 209 may be a conventional mechanism for coupling a laser beam to an optical fiber. Such mechanisms include lenses, prisms, collimators etc. Back scattering module 210 is comprised of the necessary optics for isolating the reflected signal. Photodetector 211, signal processor 212 and display means 213 can all be conventional devices and will vary depending on the measurement desired, the laser source, etc.

FIG. 5 depicts a guide wire of the present invention in combination with a balloon dilatation catheter 310. Balloon dilatation catheter 310, particularly when it is intended for use in a coronary artery, is relatively slender and has a substantially circular cross section with, for example, an outer diameter of the order of 0.056 inches. The inner radius of its lumens, of course, are even smaller and its main lumen may be of the order of 0.013 inches radius. The dilatation catheter 310 has a dilatation balloon 311 at its distal end and a main lumen 312 (see FIG. 5a) which is used typically to deliver liquids such as radiopaque dye or anticoagulants and also may be used to make pressure measurements. The main lumen 312 opens at an outlet 313 at the distal tip. As shown in further detail in FIG. 5a, the dilatation catheter is provided with an inflation lumen 314 which is smaller than lumen 312 and communicates with the interior 311a of the balloon 311 to inflate and deflate the balloon. The proximal end of the catheter may be provided with a Y-fitting 315 to provide communication at the proximal end of the catheter to each of the main lumen 312 and the inflation lumen 314. Balloon 311 may also be provided with radiopaque rings 316 to facilitate fluoroscopic monitoring of its progress and position.

In all embodiments of the guide wire of the present invention, the guide wire has a diameter ranging from 0.010 to 0.065 inches with a preferred diameter of 0.014 inches. Thus, the guide wire fits within the main lumen 312 of the dilatation catheter 310.

In practice, the dilatation catheter 310 is prepared with the guide wire in place extending through main lumen 312 with the distal end of the guide wire incorporating the Doppler means projecting about 2 centimeters distally of the outlet 313 of the dilatation catheter. The guide wire/dilatation catheter assembly is then pushed through an initially placed guide catheter into the coronary artery with the guide wire being used to steer the catheter towards the area of stenosis. When the position of the guide wire/dilatation catheter has been verified by, for example, the injection of an angiodye, the guide catheter is withdrawn and blood velocity measurements are taken. Since the guide wire of the present invention incorporates a laser or ultrasound Doppler means, when the device is in place in the blood vessel, each acoustic or light burst is transmitted through the blood and reflected by various structures, for example blood cells, vessel wall, plaque etc. The reflected signals are compared to a master oscillatory signal if the Doppler means uses ultrasonic transducer means or a master oscillatory signal if a laser Doppler means is used. The difference between the master signal and the reflected signal is the Doppler shift, which is determined by the well known Doppler equation.

While the invention has been described in terms of specific embodiments, it is to be understood that these embodiments are not intended to be limiting and the scope of the invention is only to be determined by the scope of the appended claims.

We claim:

1. A guide wire comprising
   (a) an elongated wire body having a distal portion, said wire body comprising a relatively straight central wire having a proximal and a distal portion, and a helically coiled wire spring surrounding said central wire, said relatively straight central wire and said helically coiled wire spring forming a guiding wire for steering said guide wire, said central wire and said helically coiled wire spring both comprised of a conductive material, and means for insulating said central wire and said wire spring from each other,
   (b) Doppler means for transmitting signal and for receiving a reflected signal, said Doppler means comprising a single piezoelectric transducer attached to said wire body adjacent said distal portion, said central wire and said wire spring being electrically connected to said piezoelectric transducer, whereby said central wire and said helically coiled wire spring serve as electrical leads to said piezoelectric transducer, said guide wire being adapted to steer an intravascular catheter within a blood vessel.

2. The guide wire of claim 1 wherein said guide wire has a diameter ranging from about 0.010 to about 0.065 inches.

3. The guide wire of claim 2 wherein said guide wire has a diameter of about 0.014 inches.

4. The guide wire of claim 1 wherein said Doppler means is operable in a pulsed Doppler mode wherein said single piezoelectric transducer is used which alternately acts as a transmitter and a receiver.

5. The guide wire of claim 4 wherein said single piezoelectric transducer comprises a lead-zirconium-titanate ceramic.

6. The guide wire of claim 4 wherein said piezoelectric transducer comprises a piezoelectric polymeric material.

7. The guide wire of claim 6 wherein said piezoelectric polymeric material is polyvinylidene fluoride.

8. The guide wire of claim 4 wherein said piezoelectric transducer is adapted to resonate at a range of from about 10 to about 20 Megahertz.

9. The guide wire of claim 1 wherein said piezoelectric transducer is oriented such that the ultrasonic signals is transmitted in a radial direction in relation to said distal portion of said elongated wire body.

10. The guide wire of claim 1 wherein said piezoelectric transducer is oriented such that the ultrasonic signals is transmitted in a longitudinal direction in relation to said distal portion of said elongated wire body.

* * * * *